United States Patent [19]

Feder et al.

[11] Patent Number: 5,004,771
[45] Date of Patent: Apr. 2, 1991

[54] AQUEOUS DISPERSIONS OF CROSSLINKABLE SILICONES/SILICONATES

[75] Inventors: Michel Feder, Illfurth; Jean-Marc Frances, Villeurbanne, both of France

[73] Assignee: Rhone-Poulenc Chimie, Courbevoie, France

[21] Appl. No.: 419,701

[22] Filed: Oct. 11, 1989

[30] Foreign Application Priority Data

Oct. 11, 1988 [FR] France ................. 88 13617

[51] Int. Cl.$^5$ ............................................. C08K 5/54
[52] U.S. Cl. .................................. 524/161; 524/262; 524/588; 524/730; 524/745; 428/78
[58] Field of Search ............... 524/161, 262, 588, 730, 524/745; 424/78

[56] References Cited

U.S. PATENT DOCUMENTS

| | | | |
|---|---|---|---|
| 3,294,725 | 12/1966 | Findlay et al. | 524/745 |
| 4,244,849 | 1/1981 | Saam | 524/442 |
| 4,618,645 | 10/1986 | Bauman | 524/745 |
| 4,761,454 | 8/1988 | Oba et al. | 524/588 |
| 4,816,506 | 3/1989 | Gamon et al. | 524/262 |
| 4,863,985 | 9/1989 | Pouchol et al. | 524/588 |

FOREIGN PATENT DOCUMENTS

| | | |
|---|---|---|
| 0169098 | 1/1986 | European Pat. Off. . |
| 0202494 | 11/1986 | European Pat. Off. . |
| 0266729 | 5/1988 | European Pat. Off. . |
| 0277740 | 8/1988 | European Pat. Off. . |
| 0332544 | 9/1989 | European Pat. Off. . |

Primary Examiner—Veronica P. Hoke
Attorney, Agent, or Firm—Burns, Doane, Swecker & Mathis

[57] ABSTRACT

Aqueous dispersions of a silicone crosslinkable into elastomeric state by elimination of water therefrom, include:

(A) 100 parts of an oil-in-water emulsion of an α,ω-(dihydroxy)polydiorganosiloxane, stabilized with an anionic and/or nonionic surfactant;
(B) 0.1 to 15 parts of an organosiliconate; and
(C) 5 to 250 parts of a nonsiliceous inorganic filler material; and such emulsion having a pH higher than 7 and a solids content of at least 40%; the subject emulsions are especially adapted for the production of silicone elastomer seals for the coating of food packaging materials.

14 Claims, No Drawings

AQUEOUS DISPERSIONS OF CROSSLINKABLE SILICONES/SILICONATES

CROSS-REFERENCE TO COMPANION APPLICATION

Copending application, Ser. No. 419,719 filed of even date, assigned to the same assignee and having due title "Aqueous Dispersions of Crosslinkable Silicone Alkenyloxysilanes".

BACKGROUND OF THE INVENTION

1. Field of the Invention

The present invention relates to novel aqueous dispersions of a siliconate-based silicone, which novel dispersions are crosslinkable into elastomeric state by elimination of water therefrom.

2. Description of the Prior Art

U.S. Pat. No. 2,891,920 describes a process for emulsion polymerization of polydiorganosiloxanes utilizing an acidic or basic catalyst in the presence of anionic, cationic or nonionic surface-active agents. The '920 patent relates that the emulsions obtained are stable in storage and, after addition of fillers, can be used to formulate paints for providing continuous coatings by elimination of water therefrom.

U.S. Pat. No. 3,294,725 describes, in particular, the use of dodecylbenzenesulfonic acid to polymerize polydiorganosiloxanes in emulsion. This '725 patent observes that to obtain stable emulsions it is desirable to adjust the pH of such emulsions to a value of approximately 7. It also relates that an elastomeric coating can be obtained from these neutralized emulsions, to which colloidal silica and a polyalkoxysilane have been added.

U.S. Pat. No. 3,360,491 is similar to the '725 patent, except that dodecylbenzenesulfonic acid is replaced with lauryl hydrogen sulfate.

U.S. Pat. No. 3,697,469 describes a particular process for emulsion polymerization of polydiorganosiloxanes and indicates the possibility of adding colloidal silica and a tin salt to the emulsion in order to provide an elastomeric coating by water evaporation.

French Patent FR-A-2,110,358 describes a silicone emulsion having a pH of between 6.5 and 9, crosslinking to an electrically conductive elastomer after evaporation of water and incorporating carbon black. The emulsion, additionally containing a tin salt and a polyalkoxysilane, is not stable in storage and must be stored in two separate packages (two-component emulsion).

U.S. Patents Nos. 4,221,688 and 4,244,849, and French Patent FR-A-2,463,163, describe storage-stable silicone emulsions comprising:

(i) an anionically stabilized emulsion of an $\alpha,\omega$-(dihydroxy)polydiorganosiloxane polymer;
  (ii) a siliceous filler;
  (iii) a tin salt; and
  (iv) optionally, a nonreinforcing filler.

The siliceous filler may be a colloidal silica (U.S. Pat. No. 4,221,688), sodium silicate (U.S. Pat. No. 4,244,849) or an amorphous silica powder (FR-A-2,463,163).

In comparison with the known aqueous emulsions (dispersions) of the prior art, these three patents offer, on the one hand, that to obtain a storage-stable single-component emulsion, the emulsion must be stored at an alkaline pH higher than 8.5 or 9, preferably higher than 10 and, on the other hand, a tin salt must be incorporated in the emulsion to shorten to a few days the emulsion ripening or aging stage required to provide a crosslinkable dispersion.

U.S. Pat. No. 3,355,406 describes a silicone latex of an $\alpha,\omega$-(dihydroxy)polydiorganosiloxane, preferably prepared by emulsion polymerization, and of a sesquisiloxane resin including $RSiO_{1.5}$ recurring units (R = hydrocarbon residue). The latex may additionally comprise a metal curing catalyst and an alkyltrialkoxysilane.

In U.S. Pat. No. 4,554,187, the silicone resin used in combination with the $\alpha,\omega$-(dihydroxy)polydiorganosiloxane is a reactive resin of low molecular weight, containing alkoxy or acyloxy groups.

In patent application Ser. No. EP-A-266,729, the silicone resin used in combination with the $\alpha,\omega$-(dihydroxy)polydiorganosiloxane and with the curing catalyst is a siliconate.

A silicone resin comprising up to 10% by weight of hydroxyl groups may be used in combination with this siliconate.

Catalyst-free silicone latices are described in Patents EP-A-166,396 and EP-A-169,386, as well as in EP-A-277,740, but they do not comprise any silicone resins.

Examination of the prior art indicates that most of the aqueous silicone dispersions comprise a curing catalyst which is a metal salt, generally an organotin salt.

However, the presence of such metal salt is not without disadvantages. It may be, in fact, the source of an inadequate storage stability. Furthermore, for coating medications and for coating articles destined to be in contact with foodstuffs and beverages, such as cork stoppers, serious need continues to exist in this art for organopolysiloxane compositions capable of crosslinking into a silicone elastomer without the requirement for a metal curing catalyst.

SUMMARY OF THE INVENTION

Accordingly, a major object of the present invention is the provision of novel aqueous dispersions of a silicone, devoid of any curing catalyst, which novel dispersions crosslink properly into elastomeric state upon elimination of water therefrom.

Another object of the present invention is the provision of novel aqueous dispersions of the above type, which are stable in storage, of a silicone which properly crosslinks sufficiently quickly into an elastomer by elimination of water therefrom at ambient temperature, the elastomer formed retaining and even improving its mechanical properties upon aging thereof.

Another object of this invention is the provision of novel aqueous silicone dispersions of the above type, the stage of ripening of which can be carried out at a relatively low temperature (20°-60° C).

Another object of the present invention is the provision of novel aqueous silicone dispersions of the above type, ultimately providing an elastomer additionally exhibiting an improved flame resistance.

Yet another object of this invention is the provision of novel aqueous silicone dispersions of the above type that are crosslinkable into elastomers exhibiting satisfactory adhesiveness to a variety of substrates, in particular to glass, concrete and metals (steel, aluminum, etc.).

Briefly, the present invention features novel aqueous dispersions of a silicone that are crosslinkable into elastomeric state by elimination of water therefrom under ambient conditions, said novel aqueous dispersions comprising:

(A) 100 parts by weight of an oil-in-water type emulsion of an α,ω-(dihydroxy)polydiorganosiloxane, stabilized with at least one surface-active agent selected from among anionic and nonionic surface-active agents and mixtures thereof;

(B) 0.1 to 15 parts by weight, calculated as the solids content, of an alkali metal or alkaline earth metal organosiliconate in aqueous solution; and (C) 5 to 250 parts by weight of a nonsiliceous inorganic filler material;

the said dispersions having a pH higher than 7, preferably ranging from 8 to 13, and a solids content of at least 40%.

DETAILED DESCRIPTION OF THE PREFERRED EMBODIMENTS OF THE INVENTION

More particularly according to the present invention, the α,ω-(dihydroxy)polydiorganosiloxanes (A) must have a viscosity of at least 100 mPa.s at 25° C., preferably of at least 50,000 mPa.s.

Indeed, an elastomer is in fact obtained in the case of viscosities higher than 50,000 mPa.s, exhibiting a combination of appropriate mechanical properties, in particular with regard to Shore A hardness and elongation.

Furthermore, the higher the viscosity, the more the mechanical properties are retained as the elastomer ages.

According to the present invention, the preferred viscosities range from 50,000 to 1,500,000 mPa.s at 25° C.

The organic radicals of the α,ω-(dihydroxy)polydiorganosiloxanes are monovalent hydrocarbon radicals containing up to 6 carbon atoms, optionally substituted by cyano or fluoro groups. The substituents generally incorporated, because of their availability in industrial products, are methyl, ethyl, propyl, phenyl, vinyl and 3,3,3-trifluoropropyl radicals. In general, at least 80% of the number of such radicals are methyl radicals.

The preferred polymers according to the present invention are the α,ω-(dihydroxy)polydiorganosiloxanes prepared by the anionic polymerization process described in the aforementioned U.S. Pat. Nos. 2,891,920 and, especially, 3,294,725. The polymer obtained is stabilized anionically with a surface-active agent which, as per U.S. Pat. No. 3,294,725, is preferably the alkali metal salt of an aromatic hydrocarbon sulfonic acid, the free acid also serving as a polymerization catalyst.

The preferred catalyst and surface-active agent are dodecylbenzenesulfonic acid and its alkali metal salts, in particular its sodium salt. Other anionic or nonionic surface-active agents may be added, if desired. However, this addition is unnecessary because, according to U.S. Pat. No. 3,294,725, the amount of anionic surface-active agent resulting from the neutralization of the sulfonic acid is sufficient to stabilize the polymer emulsion. This amount is generally less than 3%, preferably 1.5% of the weight of the emulsion.

This emulsion polymerization process is particularly advantageous because it enables the emulsion (A) to be directly prepared. Furthermore, this process offers the ability to produce α,ω-(dihydroxy)polydiorganosiloxane emulsions (A) of very high viscosity without difficulty.

To prepare the emulsion (A), it is also possible to begin with an already polymerized α,ω-(dihydroxy)polydiorganosiloxane and to then convert it into an aqueous emulsion by stabilizing the emulsions with an anionic and/or nonionic surface-active agent according to a process which is well known to this art and described in detail in the literature (see, for example, FR-A-2,064,563, FR-A-2,094,322, FR-A-2,114,230 and EP-A-169,098).

According to this process, the α,ω-(dihydroxy)polydiorganosiloxane polymers are mixed merely by stirring them with the anionic or nonionic surface-active agent, it being possible for the latter to be in aqueous solution. Then water is added, if necessary, and the entire mixture is converted into a fine and homogeneous emulsion by passing same through a conventional colloid mill.

The millbase obtained is then diluted with an appropriate amount of water and an emulsion (A) stabilized with an anionic or nonionic surface-active agent and stable in storage is thus obtained.

The amount of anionic and nonionic surface-active agent which can be employed is that commonly employed in the emulsification process, in particular those described in the aforementioned patents and in U.S. Pat. No. 2,891,920.

According to the present invention, the preferred anionic surface-active agents are an alkali metal salt of an aromatic hydrocarbon sulfonic acid and the preferred nonionic surface-active agents are polyoxyethylenated alkylphenols. These nonionic surface-active agents are, of course, the same as those which can be optionally added to the emulsions (A) produced by emulsion polymerization as indicated above.

The emulsion (A) prepared by emulsion polymerization or by emulsification of the silicone polymer is in the form of an oil-in-water emulsion and preferably has a solids content higher than 45% by weight.

From 0.to 15 parts, preferably from 0.5 to 5 parts, calculated as the solids content, of an alkali metal or alkaline earth metal organosiliconate (B) in aqueous solution are incorporated per 100 parts of emulsion (A).

These alkali metal or alkaline earth metal organosiliconates are known materials, most of which are available commercially. The most common ones are sodium or potassium methylsiliconates with a solids content of approximately 30% to 60%.

The alkali metal organosiliconates can be prepared, for example, by hydrolysis of the corresponding organosilanes containing 3 hydrolyzable groups, such as halogen atoms or alkoxy radicals, followed by dissolving the product obtained in a solution of a strong inorganic base, in such proportions as to provide at least one equivalent of base per silicon atom (see, for example, U.S. Pat. Nos. 2,441,422, 2,441,423 and 2,507,200).

Another constituent of the emulsion according to the invention is the addition of 5 to 250 parts, preferably of 10 to 200 parts, of a semireinforcing or packing inorganic filler (C).

The fillers (C) have a particle size which generally ranges from 0.001 to 300 μm and a BET surface area lower than 100 m$^2$/g.

Examples of fillers (C) which can be employed either alone or in admixture are: carbon black, titanium dioxide, aluminum oxide, hydrated alumina, expanded vermiculite, unexpanded vermiculite, calcium carbonate, zinc oxide, mica, talc, iron oxide, barium sulfate and slaked lime.

These fillers (C) are introduced into the emulsion in dry powder form, for example merely by mixing.

According to an alternative embodiment of the invention, it has been found that if the filler (C) is substantially only a filler selected from among hydrated alumina, expanded vermiculite, or unexpanded vermiculite in a proportion of 5 to 250 parts, preferably of 50 to 200 parts, per 100 parts of emulsion (A), then an elastomer is obtained having a flame resistance which is particularly high and which cannot be obtained with the other of the above-mentioned categories of filler (C), in particular with aluminum oxide or unhydrated alumina. Ceramic or aramid fibers, as described in EP-A-212,827, may also be incorporated.

In another embodiment of the invention, it is possible additionally to incorporate, per 100 parts of emulsion (A), a siliceous additive (D) selected from among sodium silicate (0.3 to 30 parts), and a reinforcing or semi-reinforcing siliceous filler (1 to 150 parts).

These siliceous fillers are selected from among colloidal silica, pyrogenic and precipitated silica powders or a mixture thereof. Pyrogenic silica is preferred. It is also possible, however, to employ semireinforcing siliceous fillers such as diatomaceous earths or ground quartz.

The sum of the parts of (C)+(D) must be less than 300 parts per 100 parts of emulsion (A).

Pyrogenic and precipitated silica powders are well known; they are employed, in particular, as fillers in silicone elastomer compositions capable of being vulcanized to a silicone rubber when heated. These powders have a mean particle size which is generally below 0.1 $\mu$m and a BET specific surface area higher than 50 $m^2/g$, preferably ranging from 150 to 350 $m^2/g$.

The incorporation of this siliceous additive (D) in the emulsion (A) by any suitable means, in particular by stirring, considerably increases the viscosity of the emulsion (A), which is then pasty in character.

Indeed, it has now been found that the addition of this siliceous additive (D) is sufficient to impart a more or less pronounced "thixotropic" character to the emulsion. When removed from, for example, a storage cartridge, the emulsion adheres without flowing, even to a vertical substrate, and cures into elastomeric state by evaporation of water at ambient temperature. A nonflowing emulsion can also be obtained by employing as a filler (C) calcium carbonate whose mean particle diameter is smaller than 0.1 $\mu$m. Slight heating (to approximately 40° to 80° C.) of the composition, to accelerate water evaporation, is also within the ambit of the present invention.

The aqueous dispersions may also comprise a hydroxylated silicone resin (B).

In addition, from 1 to 20 parts, preferably from 2 to 10 parts, of a hydroxylated silicone resin (E), calculated as the solids content, may be incorporated per 100 parts of emulsion (A).

The hydroxylated silicone resin (E) has a weight content of hydroxyl groups of from 0.1% to 10%, preferably from 1% to 6%.

This resin (E) contains, per molecule, at least two different recurring units selected from among those of the formulae: $R_3SiO_{0.5}$ (M unit), $R_2SiO$ (D unit), $RSiO_{1.5}$ (T unit) and $SiO_2$ (Q unit).

The M, D, T and Q units are distributed such as to provide a molar ratio R/Si lower than 2, preferably lower than 1.8, to exclude linear polydiorganosiloxanes.

The radicals R are selected from among $C_1$-$C_6$ alkyl, vinyl, phenyl and 3,3,3-trifluoropropyl radicals.

Methyl, ethyl, isopropyl, tert-butyl and n-hexyl radicals are exemplary of the alkyl radicals R.

These silicone resins are well known branched organopolysiloxane polymers, the processes for the preparation of which are widely described in the patent literature.

MQ resins, MDQ resins, TD resins and MDT resins are representative examples of resins which can thus be employed.

Resins which are solid or liquid at ambient temperature can be used. These resins can be incorporated in the aqueous emulsions as such, in solution in an organic solvent or a silicone oil, or else in the form of aqueous emulsions.

Aqueous emulsions of silicone resins which can be employed are described, for example, in U.S. Pat. Nos. 4,028,339, 4,052,331, 4,056,492, 4,525,502 and 4,717,599.

Various additives enabling the properties of the dispersions and of the elastomers formed from the dispersions by elimination of water to be modified may be added, if desired, to the dispersions in accordance with the present invention. In particular, it is possible to incorporate an additive (F) selected from among organotrialkoxysilanes such as, for example, vinyltrimethoxysilane, alkyl silicates such as methyl silicate or ethyl silicate or the product of their partial hydrolysis, namely, alkyl polysilicates such as methyl polysilicate and ethyl polysilicate in a proportion of 0.1 to 20 parts of additive (F) per 100 parts of emulsion (A). The additive (F) makes it possible to improve the cohesion of the elastomeric material obtained after elimination of water.

The organotrialkoxysilanes and the alkyl silicates preferably correspond to the general formula:

$$R''_a Si(OR')_{4-a}$$

in which R' is an alkyl radical containing from 1 to 4 atoms, R" is R' or vinyl and a is 1 or 0.

Antifungal and antimoss agents, as well as agents imparting thixotrophy, such as carboxymethyl cellulose, xanthan gum and polyvinyl alcohol, are other examples of additives.

The dispersions according to the invention can be prepared in the following manner:

The starting material is an emulsion (A) prepared either by the emulsion polymerization process, and an emulsion stabilized by an anionic and optionally nonionic surface-active agent is produced, or by the process of emulsifying the $\alpha,\omega$-(dihydroxy)polydiorganosiloxane, and emulsion stabilized by an anionic and/or nonionic surface-active agent is produced.

To prepare the dispersions according to the invention, it is recommended to first add the organosiliconate (B) to the emulsion (A) at ambient temperature and then, if need be, the pH of the mixture is adjusted to a value higher than 7 using an inorganic or organic base. The organic base employed may be primary amines such as diethylamine. However, in a preferred embodiment of the invention, the pH is adjusted by means of an adapted amount of an inorganic base introduced in the form of an aqueous solution, preferably selected from among solutions of alkali metal and alkaline earth metal hydroxides such as sodium hydroxide, potassium hydroxide, and solutions of calcium hydroxide, barium hydroxide and magnesium hydroxide. However, alkaline earth metal hydroxides may be introduced directly in solid form.

The fillers (C) and, if desired, the siliceous fillers (D), the resin (E) as such, or in solution in an organic solvent or in a silicone oil, or else in the form of an aqueous emulsion, and the adhesion promoter (F) are added.

A trimethylsilyl-blocked polydimethylsiloxane having a viscosity of from 100 to 5,000 mPa.s at 25° C. may be employed as a silicone oil used in combination with the resin (E).

The final emulsion obtained is homogenized and then degassed and is next packaged in a package which is impervious to atmospheric oxygen and to water vapor.

The constituents (A), (B), (C) and, if desired, (D), (E) and (F) are mixed in such amounts that the final emulsion has a solids content which is higher than 40%, preferably higher than 60%, but generally lower than 90%. The preferred pH range is from 8 to 13.

The dispersions according to the invention may be employed as a paint which can be crosslinked into thin layer form. They then preferably have a solids content of from 40% to 70%.

To determine the solids content, 2 g of dispersion are placed in an aluminum weighing dish, which is heated to 150° C. for one hour in an oven with air circulation. After cooling, the dish is weighed again and the percentage of material remaining from the initial 2 g is determined, representing the solids content.

In a preferred embodiment of the invention, after being prepared, the dispersion is subjected to a ripening stage at ambient temperature, of a few hours to a few days.

This ripening stage entails merely permitting the dispersion to stand protected against atmospheric oxygen before it is used.

The dispersions according to the invention can be employed for producing silicone elastomer seals, in particular for the building and construction industry.

These dispersions can also be employed for coating various pharmaceutical or plant-protective active substances formulated in a solid form (pellets, tablets, pills, and the like), for coating corks used for sealing wine and spirit bottles, to produce coatings of kitchen articles and, generally, of articles in contact with foodstuffs (for example, bread pans).

Known coating methods can be employed, in particular the methods of brush- and dip-(immersion)-coating, spraying techniques, fluidized-bed coating techniques and immersion-coating techniques.

In the case of cork coatings, a recommended technique is the dipping technique which comprises immersing the corks in the dispersion, which wets the surface of the corks, and then evaporating off the water.

The coating obtained represents 20 to 50 mg of elastomer per 100 cm$^2$ of cork surface area. This layer makes it easier for the cork to slide into the neck of the bottle during the bottling and prevents "running", that is to say, leakages of liquid between the neck and the cork.

A completely surprising and unexpected specific advantage of the dispersions according to the invention, compared with the known dispersions containing a metal curing catalyst, generally an organotin compound, in particular compared with the dispersions described in EP-A-266,729, is that the dispersions of the invention produce elastomers which exhibit a retention and even an improvement in their mechanical properties during normal or accelerated aging. On the other hand, the elastomers produced from known dispersions containing a metal curing catalyst exhibit, predictably, a deterioration of all of their mechanical properties over the course of their normal or accelerated aging.

This specific advantage of the dispersions according to the invention is reflected, in particular, in an increase in tensile strengths and elongations at break, whose tendency is such that an elastomer of improved quality is obtained in the course of its aging. This phenomenon would not have been expected, especially since the dispersions according to the invention have a setting time and ripening period which are wholly acceptable and result in elastomers exhibiting final mechanical properties similar to the elastomers produced from known dispersions comprising a metal catalyst.

In order to further illustrate the present invention and the advantages thereof, the following specific examples are given, it being understood that same are intended only as illustrative and in nowise limitative.

In said examples to follow, all parts and percentages are given by weight, unless otherwise indicated.

EXAMPLE 1

An emulsion (A) was prepared by emulsion polymerization of an $\alpha,\omega$-(dihydroxy)polydimethylsiloxane oil having a viscosity of 100 mPa.s at 25° C. in the presence of dodecylbenzenesulfonic acid.

When the oil viscosity reached $1.5 \times 10^6$ mPa.s at 25° C., the polymerization was terminated by neutralizing the catalyst.

7 parts of a solution of potassium methylsiliconate having a solids content of 40% were added to 170 parts of emulsion (A) having a solids content of 58% and the mixture homogenized at 25° C.

After 10 minutes of homogenization, 100 parts of $CaCO_3$ having a mean particle size of 70 nanometers were added.

The final dispersion had a solids content of 73.2% and had a pH higher than 9.

This dispersion was homogenized for 30 minutes and was then packaged in a packaging material which was impervious to atmospheric oxygen and to water vapor.

After 5 days of storage, the dispersion was spread with a doctor blade to form a 2-mm thick film which was permitted to dry for 7 days at ambient temperature (20° C).

The following mean mechanical properties were measured on a first batch of dried films:

(a) Shore A hardness (SAH) according to ASTM standard D-2240;

(b) tensile strength (TS) according to AFNOR standard T 46 002, corresponding to ASTM standard D 412, in MPa;

(c) elongation at break (EB) in % according to AFNOR standard T 46 002;

(d) the elasticity modulus (EM) at 100% elongation, according to AFNOR standard T 46 002, in MPa.

The mechanical properties after a natural aging of the films at ambient temperature were measured on a second batch of dried films.

The mechanical properties obtained are reported in the Table below.

From the Table, it will be seen that after 6 months of aging, the elastomer retained substantially the same values in the case of SAH and EM, and markedly improved the TS and the EB.

To assess the adhesiveness, a 4-mm thick bead of aqueous dispersion was deposited onto a glass or concrete support. After 12 days, the adhesiveness of the elastomer formed was assessed by pulling the bead by hand.

The adhesiveness was good on both supports, it having been impossible to part the bead from its support by hand.

EXAMPLE 2

The operating procedure of Example 1 was repeated exactly, except that 7 parts by weight of vinyltrimethoxysilane were added after the addition of the siliconate. The pH of the final dispersion was 11.

The mechanical properties are reported in the Table below.

The adhesiveness to a support made of glass or concrete was good.

EXAMPLE 3

The operating procedure of Example 1 was repeated exactly, except that 5 parts by weight of magnesium hydroxide were also added after the addition of siliconate. The pH of the final dispersion was 12.

The mechanical properties are reported in the Table below.

Adhesiveness to a support made of glass or concrete was good.

EXAMPLE 4

The operating procedure of Example 1 was repeated exactly, except that:

(i) the starting material was an emulsion (A) in which the silicone oil had a viscosity of $10^6$ mPa.s at 25° C.;

(ii) 2 parts by weight of ethyl polysilicate (ethyl silicate 40°, marketed by Union Carbide Corporation) were also added; and (iii) the second batch of films was subjected to 7 days of aging at 50° C. in a ventilated oven.

The mechanical properties obtained are reported in the Table below.

Adhesiveness to a support made of glass or concrete was good.

From the Table, it will be seen that the mechanical properties were improved after accelerated aging.

TABLE

| EXAMPLES | 1 | 2 | 3 | 4 |
|---|---|---|---|---|
| SAH | | | | |
| 7 days at 20° C. | 14 | 19 | 12 | 25 |
| 6 months at 20° C. | 12 | — | — | — |
| 7 days at 50° C. | — | — | — | 28 |
| TS (MPa) | | | | |
| 7 days at 20° C. | 0.33 | 1.15 | 0.63 | 0.45 |
| 6 months at 20° C. | 0.63 | — | — | — |
| 7 days at 50° C. | — | — | — | 1.08 |
| EB (%) | | | | |
| 7 days at 20° C. | 540 | 1.221 | 936 | 190 |
| 6 months at 20° C. | 980 | — | — | — |
| 7 days at 50° C. | — | — | — | 484 |
| EM (MPa) | | | | |
| 7 days at 20° C. | 0.19 | 0.26 | 0.22 | 0.96 |
| 6 months at 20° C. | 0.17 | — | — | — |
| 7 days at 50° C. | — | — | — | 0.44 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A composition of matter which comprises an aqueous dispersion of a silicone crosslinkable into elastomeric state by elimination of water therefrom under ambient conditions, said silicone dispersion comprising:
   (A) 100 parts by weight of an oil-in-water emulsion of an α,ω-(dihydroxy)polydiorganosiloxane, stabilized with at least one anionic or nonionic surface-active agent, or admixture thereof;
   (B) 0.to 15 parts by weight, calculated as the solids content, of an alkali or alkaline earth metal organosiliconate in aqueous solution; and
   (C) 5 to 250 parts by weight of a nonsiliceous inorganic filler material; and said dispersion having a pH higher than 7 and a solids content of at least 40%, said aqueous dispersion being devoid of any curing catalyst.

2. The aqueous silicone dispersion as defined by claim 1, said emulsion (A) having a solids content of at least 45% by weight.

3. The aqueous silicone dispersion as defined by claim 1, said filler material (C) comprising hydrated alumina, alumina, calcium carbonate, expanded vermiculite, unexpanded vermiculite, carbon black, zinc oxide, titanium dioxide, mica, talc, iron oxide, barium sulfate or slaked lime.

4. The aqueous silicone dispersion as defined by claim 3, comprising a calcium carbonate having a mean particle diameter smaller than 0.1 μm.

5. The aqueous silicone dispersion as defined by claim 1, comprising:
   (A) 100 parts of an oil-in-water emulsion of an α,ω-(dihydroxy)polydiorganosiloxane having a viscosity of from 50,000 to 1,500,000 mPa.s at 25° C., stabilized with an alkali metal salt of an aromatic hydrocarbon sulfonic acid or a polyoxyethylenated alkylphenol;
   (B) 0.5 to 5 parts of an organosiliconate; and
   (C) 50 to 200 parts of an inorganic filler material; and said dispersion having a pH of from 8 to 13 and a solids content of at least 60%.

6. The aqueous silicone dispersion as defined by claim 1, further comprising, per 100 parts of the emulsion (A), a siliceous additive (E) which comprises sodium silicate or a reinforcing or semireinforcing siliceous filler, with the proviso that the sum of the parts of (C)+(E) is less than 300 parts per 100 parts of (A).

7. The aqueous silicone dispersion as defined by claim 1, further comprising, per 100 parts of emulsion (A), 1 to 20 parts by weight of a hydroxylated silicone resin (E) containing at least two different recurring units per molecule, said recurring units including those of the formulae: $R_3SiO_{0.5}$, $R_2SiO$, $RSiO$, $RSiO_{1.5}$ and $SiO_2$, in which the radicals R, which may be identical or different, are each a vinyl, phenyl or 3,3,3-trifluoropropyl radical, or a linear or branched chain alkyl radical containing from 1 to 6 carbon atoms, and said resin having a weight content of hydroxyl groups ranging from 0.1 to 10%.

8. The aqueous silicone dispersion as defined by claim 1, further comprising, per 100 parts of emulsion (A), from 0.01 to 20 parts of an additive (F) which comprises an organotrialkoxysilane, alkyl silicate or alkyl polysilicate.

9. The aqueous silicone dispersion as defined by claim 1, further comprising an aqueous solution of an alkali or alkaline earth metal hydroxide.

10. The aqueous silicone dispersion as defined by claim 9, comprising an alkaline earth metal hydroxide introduced directly in a solid form.

11. A process for the preparation of the aqueous silicone dispersion as defined by claim 1, comprising:
  (1) admixing the emulsion (A) and the organosiliconate (B);
  (2) adding the nonsiliceous filler (C) to such admixture; and
  (3) optionally adjusting the pH of the mixture to a value higher than 8.5, with the proviso that the total amount of water employed is such that the solids content of the final emulsion is at least 40%.

12. The aqueous silicone dispersion as defined by claim 1, in cured elastomeric state.

13. A substrate coated with the aqueous silicone dispersion as defined by claim 1.

14. The coated substrate as defined by claim 13, said substrate comprising a pharmaceutical or agricultural chemical, a food wrapping material, or a cork item.

* * * * *